United States Patent
Pörschke et al.

(10) Patent No.: US 11,279,715 B2
(45) Date of Patent: Mar. 22, 2022

(54) PROCESS FOR REMOVING RADIOACTIVE ISOTOPES FROM AQUEOUS FLUIDS BY FLUORINE CONTAINING REAGENTS, FLUORINE CONTAINING, WATER-INSOLUBLE SALTS OF THE RADIOACTIVE ISOTOPES, AND THEIR USE AS THERAPEUTIC AGENTS

(71) Applicant: STUDIENGESELLSCHAFT KOHLE MBH, Mülheim (DE)

(72) Inventors: Klaus-Richard Pörschke, Mülheim an der Ruhr (DE); David Pollak, Ratingen (DE)

(73) Assignee: STUDIENGESELLSCHAFT KOHLE MBH

( * ) Notice: Subject to any disclaimer, the term of this patent is extended or adjusted under 35 U.S.C. 154(b) by 0 days.

(21) Appl. No.: 16/083,043

(22) PCT Filed: Mar. 7, 2017

(86) PCT No.: PCT/EP2017/055367
§ 371 (c)(1),
(2) Date: Sep. 7, 2018

(87) PCT Pub. No.: WO2017/153436
PCT Pub. Date: Sep. 14, 2017

(65) Prior Publication Data
US 2019/0092793 A1    Mar. 28, 2019

(30) Foreign Application Priority Data

Mar. 9, 2016   (EP) ..................... 16159522
Apr. 26, 2016  (DE) ............. 10 2016 207 067.3
Jul. 12, 2016  (DE) ............. 10 2016 112 769.8

(51) Int. Cl.
| | | |
|---|---|---|
| *C07F 5/02* | (2006.01) | |
| *G21F 9/12* | (2006.01) | |
| *G21F 9/00* | (2006.01) | |
| *A61K 31/69* | (2006.01) | |
| *A61L 2/16* | (2006.01) | |
| *C22B 3/42* | (2006.01) | |
| *C22B 26/10* | (2006.01) | |

(52) U.S. Cl.
CPC .............. *C07F 5/02* (2013.01); *A61K 31/69* (2013.01); *A61L 2/16* (2013.01); *C22B 3/42* (2013.01); *C22B 26/10* (2013.01); *G21F 9/00* (2013.01); *G21F 9/12* (2013.01); *Y02P 20/582* (2015.11)

(58) Field of Classification Search
None
See application file for complete search history.

(56) References Cited

U.S. PATENT DOCUMENTS

| 4,790,960 A | 12/1988 | Heckmann et al. |
| 6,169,208 B1 | 1/2001 | Lee |
| 6,590,009 B1 | 7/2003 | Priou |
| 8,270,554 B2 | 9/2012 | Meikrantz et al. |

FOREIGN PATENT DOCUMENTS

| EP | 1 362 860 A1 | 11/2003 |
| WO | 00/09572 A1 | 2/2000 |

OTHER PUBLICATIONS

Suzuki et al. "Role of hydrophobic counteranions in the ion pair extraction of lanthanides(III) with an electrically neutral extractant" Phys. Chem. Chem. Phys., 2003, vol. 5, pp. 726-733.*
Krossing et al. "Noncoordinating Anions—Fact or Fiction? A Survey of Likely Candidates" Angew. Chem. Int. Ed., 2004, vol. 43, No. 16, pp. 2066-2090.*
International Search Report dated May 23, 2017, dated Jun. 12, 2017.
Bilir, Vural et al: "Bis(pentafluorophenylxenonium) tetrafluoroterephthalate, p-C6F5XeO(0)CC6F4C(0)0XeC6F5, a hypervalent compound with two xenon-carbon bonds", Journal of Fluorine Chemistry 2009, vol. 130, pp. 824-829.
Lancaster, Simon J. et al: "[H2N{B(C6F5)3}2]-: A New, Remarkably Stable Diborate Anion for Metallocene Polymerization Catalysts", Organometallics 2002, vol. 21, pp. 451-453.
Lau, Ka-Cheong et al: "Comparative Reactivity of Zr- and Pd-Alkyl Complexes with Carbon Dioxide", Organometallics 2013, vol. 32, pp. 6895-6898.
Lee, Stephen B. et al: "Synthesis of the Phenoxonium Cation of an α-Tocopherol Model Compound Crystallized with Non-Nucleophilic [B(C6F5)4]- and (CB11H6Br6)-Anions", Journal of The American Chemical Society 2006, vol. 128, pp. 9332-9333.
Sarkar, Mithun et al: "Room Temperature C—H Bond Activation on a [PdI—PdI] Platform", Chemical Communications 2013, vol. 49, pp. 9764-9766.
Soliman, Mohamed A.et al: "Fast and Efficient Cesium Removal From Simulated Radioactive Liquid Waste by An Isotope Dilution-Precipitate Flotation Process", Chemical Engineering Journal 2015, vol. 275, pp. 342-350.
Lesuer et al., "Improved Electrochemistry in Low-Polarity Media Using Tetrakis(pentafluorophenyl)borate Salts as Supporting Electrolytes", Angewandte Chemie Int. Ed. 2000, 39, No. 1, pp. 248-250.
Pollak, David, et al., "H2NB2(C6F5)6] Featuring an Unequivocal 16-Coordinate Cation"; J. Amer. Chem. Soc., 138: 9444-9451 (2016).

* cited by examiner

*Primary Examiner* — Joseph R Kosack
(74) *Attorney, Agent, or Firm* — Norris McLaughlin, P.A.

(57) ABSTRACT

The present invention refers to a process for removing Cs, and optionally Rb, from aqueous fluids including body fluids by fluorine containing reagents, the synthesis of fluorine containing, water-insoluble salts of said Cs isotopes and their use as therapeutic agents.

16 Claims, 3 Drawing Sheets

Figure 1:
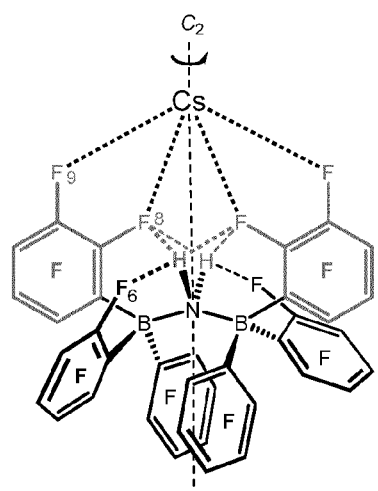

PROCESS FOR REMOVING RADIOACTIVE ISOTOPES FROM AQUEOUS FLUIDS BY FLUORINE CONTAINING REAGENTS, FLUORINE CONTAINING, WATER-INSOLUBLE SALTS OF THE RADIOACTIVE ISOTOPES, AND THEIR USE AS THERAPEUTIC AGENTS

This application is a 371 of PCT/EP2017/055367, filed Mar. 7, 2017, which claims foreign priority benefit under 35 U.S.C. § 119 of German Patent Application No. DE 10 2016 112 769.8, filed Jul. 12, 2016, German Patent Application No. DE 10 2016 207 067.3, filed Apr. 26, 2016, and European Patent Application No. 16159522.8, filed Mar. 9, 2016, the disclosures of which are incorporated herein by reference.

The present inventions refers to a process for removing radioactive isotopes, in particular Cs isotopes from aqueous fluids including body fluids by fluorine containing reagents, the fluorine containing, water-insoluble salts of said Cs isotopes and their use for diagnostic, therapeutic or technical applications. In some detail, the invention refers to an effective separation of cesium from fluids. Such fluids may be brines obtained from digestion of cesium ores, used cesium containing drilling fluids, and fluids containing Cs-131, Cs-134, Cs-135, or Cs-137 isotopes, either as solutions from a synthesis process, reprocessing process, or as wastewaters from atomic plant facilities.

Cesium is the largest, heaviest, and most electropositive of all alkali metals. In nature cesium occurs only in the form of its Cs(I) salts. The metal is relatively rare and closely associated with other alkali metals. There are deposits of Cs ores in several countries. The most important deposit is that of pollucite [$Cs(AlSi_2O_6)$] at the Tanco Mine at Bernic Lake in Manitoba, Canada, with a cesium content of 20-40 wt %. Other minerals are, inter alia, avogadrite [$(K,Cs)BF_4$] with up to 15 wt % $Cs_2O$ content and pezzottaite [$Cs(Be_2Li)Al_2Si_6O_{18}$, <8.4 wt % $Cs_2O$]. Smaller mines are the Bikita mine, Zimbabwe, and the Karibib mine, Namibia. Most of the cesium is converted into cesium formate which is used as a drilling fluid for oil and gas production. After usage, about 85% of the cesium formate is recovered and reprocessed. In addition, the unstable and radioactive isotopes Cs-131, Cs-134, Cs-135, and Cs-137 (radiocesium) are either synthesized intentionally or formed as nuclear fission byproducts in atomic plants. These may be processed for medical usage in cancer therapy or need to be separated in reprocessing plants for disposal.

The commercial production process of stable Cs-133 is mainly based on pollucite ore. The mineral is ground and then subjected to either acid digestion ($HCl$, $HBr$, $H_2SO_4$, $HF$) or alkaline decomposition (roasting with $CaCO_3$/$CaCl_2$). In both cases brines are obtained which after multiple step crystallization and re-dissolution processes yield $CsCl$, $Cs_2SO_4$ and similar salts as primary products. It is evident that separation of cesium from accompanying metals is a major problem. It is assumed that similar processes are performed for the reprocessing of radiocesium although no detailed open information appears available on this.

Various accidents in nuclear power plants (Chernobyl 1986, Fukushima 2011) have led to uncontrolled emissions of Cs-134, Cs-135, and Cs-137 with contaminations of water, landscape, and creature. Present state of the art remedy for humans and animals (domestic and livestock) involves administration of "insoluble Prussian blue" (PB), traded under the name Radiogardase-Cs (Supplier Heyl, Berlin, Germany). PB is ferric hexacyanoferrate, $Fe_4^{III}[Fe^{II}CN)_6]_3$.

Once a human is contaminated with Cs-137 and the compound is absorbed (orally, percutaneously, or respiratory) and distributed inside the body, excretion occurs only slowly, e.g., via urine. The "biological half-life" (retention time) of Cs-137 in the human body is around 80-100 days, with shorter times for adolescents (ca 62 days) and children (ca 42 days).

For the Radiogardase therapy, "Prussian blue insoluble" is administered at a dose of 3 g three times a day for adults and adolescents. Cesium ions are highly mobile in the body. They pass also into the bowels, but get readily re-absorbed again. With Prussian blue (PB) therapy, part of the cesium ions becomes absorbed by PB and becomes excreted with the feces. Applying PB therapy, the biological half-life of retention of cesium is reduced to approximately 26 days for adults, 30 days for adolescents, and 24 days for children.

Prussian blue itself is not absorbed by the body via the bowels to a noticeable extent. Of major importance is the absorption efficiency of PB towards $Cs^+$ ions, both with respect to the binding strength and the rate of absorption by the solid. Other materials for trapping $Cs^+$ ions may involve ion exchange resins and coordination by polyether or cryptate structures.

The inventors have found an alternative method to the PB treatment which is expected to further reduce the retention time of Cs-134/135/137 in living bodies, thereby reducing the probability of radiation damages.

The invention is based on (a) the finding of the extraordinary hydrophobicity of perfluorinated phenyl rings in large anionic ligands (molecular weight of the anion >500 Dalton) in complexes, (b) the finding of coordination of perfluorinated phenyl rings to bind to $Cs^+$ cations by way of chelating interaction of combinations of ortho/meta or meta/para fluorine atoms, and (c) the high preference of such binding to cesium over that to any other alkali metal ion. Therefore, such anions of suitable design associate with cesium ions to form cesium salts/complexes being insoluble in water in a surprising fashion. We will denote the relevant anions of the invention as [FAB] anions, where FAB signifies fluoroarylboronate.

In the prior art, a diborane-amide or amido-diboronate adduct is known as such from Bochmann (Bochmann, M. *Coord. Chem. Rev.* 2009, 253, 2000). As outlined by Bochmann, when sodium amide and perfluorinated triphenylborane are stirred in diethyl ether, a relatively robust diborane-amide or amido-diboronate adduct is formed. Bochmann has found that the anion is a truely weakly coordinating anion. No industrial applicability of said adduct with respect to pharmacy or cesium coordination has been disclosed.

According to the inventors, the insolubility of these cesium salts in water is based on
(a) said hydrophobicity of the anion,
(b) its suitable geometry to build a polymeric solid-state structure with $Cs^+$, and
(c) the low solvation energy of $Cs^+$ with water, as contrasted by the situation for the common alkali metals Li—K.
The inventors have originally reacted the perfluoro-triphenylborane amido adduct with CsF, assisted by sonication, to afford the solvent-free cesium salt. When [$Na(OEt_2)_4$][$H_2NB_2(C_6F_5)_6$] (1) and CsF in $CH_2Cl_2$ are sonicated at 40° C. and the precipitated NaF and the excess of CsF are removed by filtration, a clear solution is obtained. After concentrating the solution and addition of pentane, colorless cuboid crystals of solute-free $Cs[H_2NB_2(C_6F_5)_6]$ (2) separate in 74% yield in the course of several days (eq 1).

$$Na(OEt_2)_4^{\oplus}[H_2NB_2(C_6F_5)_6]^{\ominus} + CsF \xrightarrow[-NaF, -4Et_2O]{CH_2Cl_2} \tag{1}$$

1

$$Cs\begin{bmatrix} C_6F_5 & H & H & C_6F_5 \\ C_6F_5-B-N-B-C_6F_5 \\ C_6F_5 & & & C_6F_5 \end{bmatrix}$$

2

The compound shows a sharp melting point at 125° C. No obvious thermal anomaly was detected by DSC (differential scanning calorimetry). Compound 2 dissolves well in $CH_2Cl_2$ (ε=8.9) and THF (7.6) and even in solvents of low dielectric constant such as chloroform, $Et_2O$, and toluene (4.9-2.4). It is only limited soluble in MeOH (32.7) and virtually insoluble in water (78.4) and alkanes (≤2.0). The IR spectrum of 2 contains very few bands above 1715 cm$^{-1}$, with weak resonances at 3375 cm$^{-1}$ attributable to N—H stretching vibrations. Since the cation itself does not cause any bands, the series of bands at 1648 (ms), 1517 (s), 1461 (vs), 1272 (ms), 1082 (vs), 976 (vs), and 778 (ms) cm$^{-1}$ can be seen as characteristic for the $[H_2NB_2(C_6F_5)_6]^-$. The compound is exceptional for a $[H_2NB_2(C_6F_5)_6]^-$ salt in that it contains a monoatomic solute-free cation. Determination of the molecular structure revealed a novel $C_2$ symmetrical conformation of the weakly coordinating $[H_2NB_2(C_6F_5)]^-$ anion, which gives rise to an unprecedented 16-coordinate Cs$^+$ cation in a likewise unprecedented tetracosahedral arrangement of F atoms. The poor solubility of $Cs[H_2NB_2(C_6F_5)_6]$(2) allows nearly quantitative separation of Cs$^+$ from water which suggests potential applications as an effective Cs-134/135/137 remover from nuclear waste solutions, administration as an antidote for Cs-134/135/137 poisoning, and use for Cs-131 and Cs-137 radiotherapy.

In more detail for the invention, tris(pentafluorophenyl) boran is reacted with a monoanionic salt X$^-$ of a group 1 or group 2 metal cation, preferably Na$^+$, Mg$^{2+}$, or Ca$^{2+}$, or monocationic mixed salts of the latter such as Mg(OH)$^+$ or MgY$^+$ (Y=halide), with X$^-$ representing halide (preferably F$^-$ or Cl$^-$), OH$^-$, or NH$_2^-$. Thereby, salts M$^+[(C_6F_5)_3B$—X—$B(C_6F_5)_3]^-$ (M=Li, Na, K, ½Mg, MgY, Mg(OH), ½Ca, Ca(OH); X=F, Cl, OH, NH$_2$) (1) are formed (eq 2). When salts of the [FAB]$^-$ anions in water, alcohols, or ethereal solvents are reacted with acids under suitable conditions, the corresponding oxonium acids $[H(OH_2)_n]^+[FAB]^-$, $[ROH_2]^+[FAB]^-$, or $[H(OR_2)_2]^+[FAB]^-$ are formed. These are included in the selection of possible FAB reagents. M=H(OH$_2$)$^+$ can be understood as hydronium ion and the number of H$^+$-solvating H$_2$O molecules are not clearly defined. Cations involving Na, Mg, or Ca are particularly preferred, since biological or environmental side-effects are not to be expected. These salts show a high affinity for the Cs$^+$ cation, forming insoluble $Cs[XB_2(C_6F_5)_6]$ (2) precipitates (eq 3).

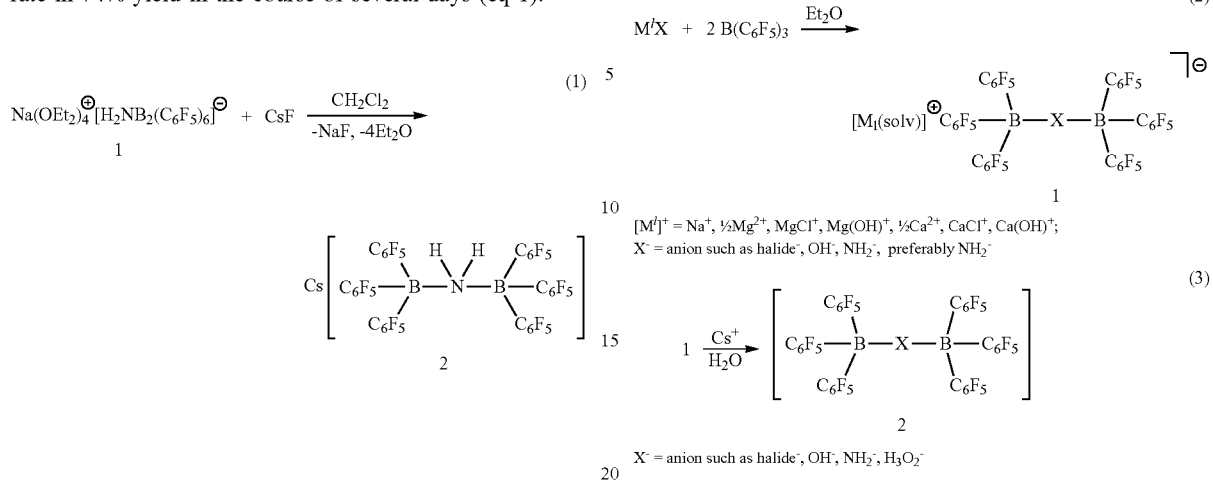

$[M^I]^+$ = Na$^+$, ½Mg$^{2+}$, MgCl$^+$, Mg(OH)$^+$, ½Ca$^{2+}$, CaCl$^+$, Ca(OH)$^+$;
X$^-$ = anion such as halide$^-$, OH$^-$, NH$_2^-$, preferably NH$_2^-$ $$1 \xrightarrow{\text{Cs}^+}{H_2O} \begin{bmatrix} C_6F_5 & & C_6F_5 \\ C_6F_5-B-X-B-C_6F_5 \\ C_6F_5 & & C_6F_5 \end{bmatrix}^{\ominus} \tag{3}$$

2

X$^-$ = anion such as halide$^-$, OH$^-$, NH$_2^-$, H$_3O_2^-$

In addition, from any aqueous Cs$^+$ source and 2 equivalents of $B(C_6F_5)_3$ (3) in water or its water adducts $(C_6F_5)_3B(OH_2)_n$ (n=1-3) (4), the compound $Cs[(C_6F_5)_3B(OH_2)$—$(HO)B(C_6F_5)_3]$ (5) is formed, since 4, in the presence of Cs$^+$, releases one H$^+$ and associates to give the anion. For the purpose of easy handling, the monohydrate $(C_6F_5)_3B(OH_2)$ (4) is used as the preferred reagent. Again, the reaction is specific for cesium, and it immediately leads to the water insoluble precipitate of $Cs[(C_6F_5)_3B(OH_2)$—$(HO)B(C_6F_5)_3]$ (5) (eq 4).

$$2 B(C_6F_5)_3 \xrightarrow{2 H_2O} 2 (C_6F_5)_3B(OH_2) \xrightarrow[-H^+]{Cs^+} \tag{4}$$

3    4

$$\begin{matrix} C_6F_5 & Cs^{\oplus} & C_6F_5 \\ C_6F_5-B-O---H-O-B-C_6F_5 \\ C_6F_5 & H & H & C_6F_5 \end{matrix}^{\ominus}$$

5

It was also found that smaller anions $[B(C_6F_5)_4]^-$, provided in the form of similar salts $[M^I(solv)]^+[B(C_6F_5)_4]^-$ (6) with $M^I$=H(OH$_2$)$_n$ (n=1-3), Li, Na, K, ½Mg, MgY, Mg(OH), ½Ca, Ca(OH) are also suitable for precipitation of cesium ions in the form of $Cs[B(C_6F_5)_4]$ (7) (Eq. 5).

$$[M^I(solv)]^+[B(C_6F_5)_4]^- \xrightarrow[H_2O]{Cs^+} Cs[B(C_6F_5)_4] \tag{5}$$

6    7

$[M^I]^+$ = H(OH$_2$)$_n^+$(n = 1-3), Na$^+$, ½Mg$^{2+}$, MgCl$^+$, Mg(OH)$^+$, ½Ca$^{2+}$, CaCl$^+$, Ca(OH)$^+$

A reaction similar to that of eq (5) works also for rubidium (Rb$^+$) and thallium (Tl$^+$), affording the new $Rb[B(C_6F_5)_4]$ (8) and known $Tl[B(C_6F_5)_4]$ (9) as water insoluble products (eqs 6a,b). Therefore, in the presence of all three cations Rb$^+$, Cs$^+$, and Tl$^+$ in water, a mixture of the compounds is obtained. However, in the absence of one or two of these ions, the reaction can be used for efficiently separating the remaining ion or ions. For example, for an aqueous solution contaminated with $Tl^+$ ions, the reaction according to eq 6b efficiently removes thallium from the aqueous fluid. For such solution contaminated with $Tl^+$ ions it appears as an unlikely case that also $Rb^+$ and/or $Cs^+$ ions are present, but if so, the ions are removed jointly. As a further application, for a brine obtained from pollucite, which is usually free from thallium and after it has been selectively depleted from cesium via eqs 3 or 4 in a preceding step, the reaction according to eq 6a is specific for rubidium. Therefore, the reaction (eq 6a) can serve to selectively separate rubidium from such aqueous fluids by precipitating $Rb[B(C_6F_5)_4]$ (8), irrespective of the other alkali metals lithium, sodium, and potassium, for which the salts $M^I[B(C_6F_5)_4]$ are strongly hydrated and, hence, water soluble. Selective separation of $Rb[B(C_6F_5)_4]$ (8) from aqueous fluids, e.g. a mineral brine, provides a substantial advantage over the current multi-step crystallization procedures.

$$[M^I(solv)]^+[B(C_6F_5)_4]^- \xrightarrow{Rb^+ / H_2O / Tl^+} \begin{array}{l} Rb[B(C_6F_5)_4] \\ 8 \\ (6a) \\ \\ Tl[B(C_6F_5)_4] \\ 9 \\ (6b) \end{array}$$

$[M^I]^+ = H(OH_2)_n^+, Na^+, \tfrac{1}{2}Mg^{2+}, MgCl^+, Mg(OH)^+, \tfrac{1}{2}Ca^{2+}, CaCl^+, Ca(OH)^+$ Thus, the present invention is directed to a:

Complex of the formula $[M^I(solv)]^+L^-$, wherein:
$M^I$ is selected from $H(OH_2)_n$, Li, Na, K, ½Mg, MgY, Mg(OH), ½Ca, Ca(OH), preferably Na, Mg or Ca, wherein Y is a halide, preferably $F^-$ or $Cl^-$, and
$L^-$ is selected from $[B(C_6F_5)_4]^-$ or $[(C_6F_5)_3B-X-B(C_6F_5)_3]^-$,
wherein X is selected from halide, $OH^-$, $O_2H_3^-$ or $NH_2^-$,
as a pharmaceutical.

In the inventive formulae, $M^I$ is intended to mean one equivalent of a metal in oxidation state one, half an equivalent of a metal in oxidation state two, or a proton solvated by water, and (solv) is intended to mean solvating ligand having O- or N-functional groups such as water, ethers, alcohols, glycol, sugars, amino acids and urea, capable of coordinating to $M^I$. In some instances, (solv) may also be absent in the formula if solvatisation is not needed.

The present invention is furthermore directed to a:

Complex as defined above as a pharmaceutical for the treatment and/or prevention of radiation damages or as antidote for the contamination of living organism with radioactive isotopes, in particular with Cs-134 and Cs-137.

Process for preparing a complex of the formula $[M^I]^+L^-$, wherein:
$M^I$ is Cs, and
$L^-$ is selected from $[B(C_6F_5)_4]^-$ or $[(C_6F_5)_3B-X-B(CF_5)_3]^-$,
wherein X is selected from halide, $OH^-$, $O_2H_3^-$ or $NH_2^-$,
wherein the process is comprising reacting a complex of the formula $[M^I(solv)]^+L^-$, wherein:
$M^I$ is selected from $H(OH_2)_n$, Li, Na, K, ½Mg, MgY, Mg(OH), ½Ca, Ca(OH), preferably Na, Mg or Ca, wherein Y is a halide,
(solv) represents a solvating ligand capable of coordinating to $M^I$, and
$L^-$ is selected from $[B(C_6F_5)_4]^-$ or $[(C_6F_5)_3B-X-B(C_6F_5)_3]^-$,
wherein X is selected from halide, $OH^-$. $O_2H_3^-$ or $NH_2^-$,
with a Cs salt in an aqueous medium.

Complex of the formula $[M^I]^+L^-$, wherein:
$M^I$ is Cs, and
$L^-$ is selected from $[B(C_6F_5)_4]^-$ or $[(C_6F_5)_3B-X-B(C_6F_5)_3]^-$,
wherein X is selected from halide, $OH^-$, $O_2H_3^-$ or $NH_2^-$.

Cs-Complex of the formula $[M^I(solv)]^+L^-$ as defined before, wherein $M^I$ is Cs in the form of a radioactive isotope, as a pharmaceutical.

Cs-Complex as defined before as a pharmaceutical for the treatment of tumor diseases, in particular malignant tumors.

Cs-Complex as defined before as a pharmaceutical in the application form for use in brachytherapy.

Use of a complex of the formula $[M^I(solv)]^+L^-$, wherein:
$M^I$ is selected from $H(OH_2)_n$, Li, Na, K, ½Mg, MgY, Mg(OH), ½Ca, Ca(OH), preferably Na, Mg or Ca, wherein Y is a halide, and
$L^-$ is selected from $[B(C_6F_5)_4]^-$ or $[(C_6F_5)_3B-X-B(C_6F_5)_3]^-$,
wherein X is selected from halide, $OH^-$, $O_2H_3^-$ or $NH_2^-$,
for the removal of cesium, in particular isotopes such as Cs-134 and Cs-137 from aqueous liquids, in particular from radioactive waste waters.

In one embodiment of the present invention in the form of a cyclic process, cesium in its (+1)-oxidation state is selectively removed from the solutions by ion-pair formation with a multi-fluorinated anion [L] and is separated in form of a water-insoluble, but ether soluble salt Cs[L]. The isolated Cs[L] is then reacted with a nonaqueous acid HA in an ethereal or alcoholic solution to precipitate the product CsA, with recovery of [L] for further usage.

The present invention suggests usage of fluorinated organic anions such as $[L]=[H_2NB_2(C_6F_5)]^-$, $[B(C_6F_5)_4]^-$, and $[(H_3O_2)B_2(C_6F_5)_6]^-$ in a cyclic reaction process, with recovery of the anion. For $[H_2NB_2(C_6F_5)_6]^-$ and $[(H_3O_2)B_2(C_6F_5)_6]^-$ the process appears 100% specific for cesium so that cesium is quantitatively and exclusively separated from all other cations in the aqueous solution. Thus, a single and fully selective separation step is necessary only to separate cesium from the other components in the form of the intermediate Cs[L]. In a second step, intermediate Cs[L] is converted into the desired product CsA, allowing recycling of [L].

The present invention makes use of the fact that the compounds Cs[L] are isolated under hydrous conditions, either first precipitated from water and then dissolved in an anhydrous ethereal or alcoholic solvent, or are directly extracted into the organic phase which then is dried. In both cases, Cs[L] in anhydrous organic solution is then degraded by reaction with nonaqueous acids HA to precipitate pure salts CsA, which are isolated as the product. The remaining ethereal or alcoholic solution retains the fluorinated anion [L] and can be used for separation of $Cs^+$ in the next reaction cycle. The stoichiometric equivalent of acid used in the cycle is transferred to the aqueous $Cs^+$ feed solution and is either neutralized by the exploited mineral, neutralized by added base (e.g., $Na_2CO_3$, $CaCO_3$), or disposed by the wastewater.

Due to the poor or even insolubility of Cs[L] in water, feed solutions of relatively low Cs concentration can be used, allowing an economic exploitation also of ores of relatively low Cs content. As most chemicals of the process are recycled, no hazardous or difficult to dispose byproducts are formed. Besides production of the introductory amount of [L] and solvent and replacement of inevitable slight losses of [L] and solvent in each cycle, the solvent and [L] are recycled in the process and only stoichiometric amounts of acid HA (e.g., HCl gas) for degradation of Cs[L] and of a base as a drying agent (e.g., $Na_2CO_3$) are consumed in the reaction process. Excess of base can serve to neutralize any acidic wastewater.

As stated above, the essential reagent in the inventive process is a compound $M^I[L]$, wherein $M^I = H(OH_2)_n^+$, n=1-3, $Li^+$, $Na^+$, $K^+$, $\frac{1}{2}(Mg^{2+})$, $MgOH+$, $\frac{1}{2}(Ca^{2+})$, $Ca(OH)^+$, preferably $Na^+$, $\frac{1}{2}(Mg^{2+})$, $\frac{1}{2}(Ca^{2+})$; and $[L]^-$ is selected from $[B(C_6F_5)_4]^-$, $[(C_6F_5)_3B-X-B(C_6F_5)_3]^-$,
wherein X is selected from $halide^-$, $O_2H_3^-$, or $NH_2^-$;
which forms a compound of formula Cs[L] in the presence of $Cs^+$ which compound precipitates from the aqueous solution.

Examples of reagents of type $M^I[L]$ are $Li[B(C_6F_5)_4]$ and $[Na(OEt_2)_4][(C_6F_5)_3B-NH_2-B(C_6F_5)_3]$. The compound $Cs[(C_6F_5)_3B(OH_2)-(HO)B(C_6F_5)_3]$ is formed from any Cs' source and 2 equivalents of $(C_6F_5)_3B(OH_2)$, since the latter, in the presence of $Cs^+$, releases one $H^+$ and associates to give the anion. Instead of $(C_6F_5)_3B(OH_2)$, the water free $(C_6F_5)_3B$ and other hydrates $(C_6F_5)_3B(OH_2)_n$ (n=2, 3) and related addition compounds of $(C_6F_5)_3B$ can also be used.

One embodiment of the inventive process for recovering Cs from aqueous liquids comprises two reaction steps to form a cyclic process. The process may be carried out following two different routes, depending on whether intermediate Cs[L] is isolated or kept dissolved in the organic phase.

The essential reactions of the process are depicted in equations (7) and (8).

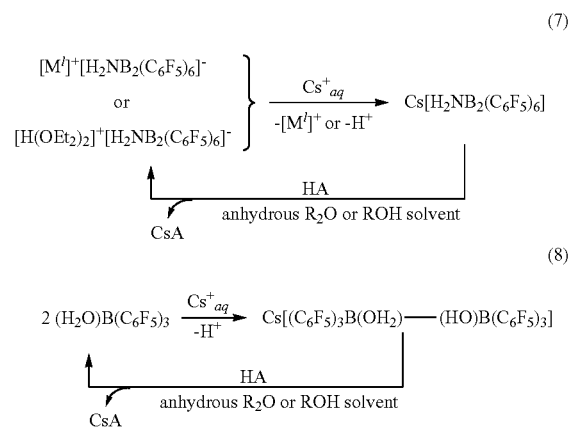

In the first step, an aqueous solution containing $Cs^+$ ions is combined with solid $M^I[L]$ or solid $(C_6F_5)_3B(OH_2)$ or a solution thereof in a volatile organic solvent which is preferably not miscible with water, such as diethyl ether, methyl tert-butyl ether (MTBE) or less preferably, an alcohol such as methanol or ethanol; preferred solvents are low boiling ethereal solvents which poorly mix with water.

The aqueous $Cs^+$ solution may be brine from the cesium mineral exploitation or any kind of waste solution, including radiocesium solutions from reprocessing plants. The solutions may be acidic or, preferably, neutral, but should not be strongly alkaline. The product of this reaction step is the ion-pair Cs[L], which depending on the given solvent condition and on concentrations may directly precipitate from the aqueous phase or may be extracted into the organic phase.

Method 1, Involving Isolation of Cs[L]:

If the reagent $M^I[L]$ or $(C_6F_5)_3B(OH_2)$ is supplied as a solid to the aqueous $Cs^+$ feed solution, the compound precipitates directly. If the reagents are supplied as a solution in an organic solvent, the organic component is distilled off from the reaction mixture to allow for an almost quantitative precipitation of Cs[L] from the then fully aqueous solution. After removal of Cs[L] by filtration, decantation, centrifugation, or a similar method the remaining aqueous solution is largely and selectively depleted from $Cs^+$. For complete $Cs^+$ removal the solution may be extracted (once) with pure ether or a chlorinated solvent. From such an extract a further fraction of solid Cs[L] may be obtained after removal of solvent. The total yield of Cs[L] obtained from combination of both isolated fractions is nearly quantitative. The remaining aqueous solution may be processed for other components or disposed. The isolated Cs[L] is dried, e.g., in a stream of air, to remove all moisture.

In the second step of method 1, the isolated Cs[L] is re-dissolved in dry diethyl ether or some other ethereal or alcoholic solvent which may serve as an acceptor for protons. A stoichiometric amount of an anhydrous acid HA is added which may be gaseous HCl and HBr, $H_2SO_4$, or a related acid; preferred is HCl gas. Addition of HA results in instantaneous precipitation of CsA, wherein A is either Cl, Br, $HSO_4$ or $\frac{1}{2}SO_4$. The salt CsA is isolated from the mixture, e.g., by filtration, washed with pure solvent to remove excess of acid, and dried in air or vacuum. The isolated CsA, e.g., CsCl, is analytically pure (99%) and represents the principal product of the separation process. The remaining acidic organic liquid contains oxonium ions such as $[(R_2O)_2H]^+$ or $[ROH_2]^+$, R being an organic group, together with the displaced anions $[L]^-$, and is fed back to step 1 of the next process cycle.

Method 2, Involving Extraction of Cs[L]:

In particular when an aqueous $Cs^+$ feed of low $Cs^+$ concentration and solutions of $M^I[L]$ or $(C_6F_5)_3B(OH_2)$ in one of the solvents specified above are given, the compound Cs[L] might be extracted into the organic phase, alternatively to method 1. In this case, the aqueous phase and the organic phase are separated and the organic phase containing Cs[L] is dried, e.g., over $Na_2CO_3$, which is then removed. The aqueous phase is processed otherwise or discarded. The anhydrous organic phase containing Cs[L] is then treated further as described in method 1.

In the following, some diagnostic, therapeutic, and technical applications are exemplarily illustrated, but not limited thereto.

Medical Diagnostic Application

For gastric and gastrointestinal processes such as emptying, the radioactive $^{129}Cs$ (half-life time $t_{1/2}$=32.1 hours) marker may be used and followed by scintillation camera. The $^{129}Cs$ isotope is produced by alpha-particle irradiation of an $^{127}I$ compound in a cyclotron. The $^{129}Cs^+$ ion must be sealed in the form of an insoluble compound to avoid absorption by the stomach or bowels; the insoluble compound is then orally administered with the food and followed by scintillation. By preparing $^{129}Cs[FAB]$ (FAB=e.g.

$H_2NB_2(C_6F_5)_6$, $B(C_6F_5)_4$, $H(HO)_2B_2(C_6F_5)_6$), $^{129}$Cs is rapidly and selectively precipitated from the nuclear reaction solution in the form of an insoluble salt which can be directly used for the indicated diagnostic purpose.

Medical Therapeutic Applications (a) Decontamination Application

For decontamination of Cs-134/135/137 poisoning of humans or animals, e.g., as a result of nuclear plant accidents (Tschernobyl, Fukushima) or "dirty bombs", direct application of, e.g., [Na(solv)][$H_2NB_2(C_6F_5)_6$], Li[$B(C_6F_5)_4$], or $(H_2O)_nB(C_6F_5)_3$ (n=1-3), e.g., in the form of polyethylene glycol solvates such as [Na(PEG-400)$_n$][$H_2NB_2(C_6F_5)_6$], is possible. The drug may be contained in capsules and swallowed orally. PEG-400 as a stabilizer may be replaced by other chelating solutes suitable for pharmaceutical applications. Additives such as PEG-400 are dissolved in the gastrointestinal tract fluids and remain physiologically inactive. Therapy follows the proven regime for insoluble Prussian blue (e.g., Radiogardase-Cs, Heyl, Berlin), which implies usage of an already present solid as an absorber for Cs$^+$ ions. As an advantage over the insoluble Prussian blue therapy, [Na(PEG-400)$_n$][$H_2NB_2(C_6F_5)_6$], [Na(PEG-400)$_n$][$B(C_6F_5)_4$], and $(H_2O)_nB(C_6F_5)_3$ are liquids in the gastrointestinal tract which allows for improved absorption kinetics of cesium ions in the bowels. When Cs$^+$ is captured by the anions, insoluble Cs[$H_2NB_2(C_6F_5)_6$] or Cs[$B(C_6F_5)_4$] precipitates. $(H_2O)_nB(C_6F_5)_3$ (n=1-3) reacts with Cs$^+$ in water by replacement of one H$^+$ to afford likewise insoluble Cs[$H(OH)_2B_2(C_6F_5)_6$]. The precipitated products are excreted with the feces. The details of the Prussian blue therapy are well documented in the literature (see also instruction leaflet of Radiogardase-Cs).

b) Cancer Treatment by the "Afterloadina Process"

Probes containing radioactive $^{137}$Cs samples (half-life time t½=30.2 years) are frequently used for cancer treatments, in particular treatments of uterus cancers, by the "afterloading process". Here, a hollow tube is placed within the cancer tissue, and a probe containing a salt of the strong emitter $^{137}$Cs is inserted into the tube for a defined time and then removed again to allow for defined radiation. While details of the treatment correspond to current medical practice, our invention refers to the production of the inserts. For the purpose of cancer treatments by the afterloading regimen, pure, robust to radiation, and easy to handle $^{137}$Cs radiation sources are necessary. These are prepared from the debris of used nuclear fuels in reprocessing plants. The problems of nuclear waste reprocessing and $^{137}$Cs separation can be substantially alleviated by isolating $^{137}$Cs[FAB] (FAB=fluoroarylboronate) salts directly and selectively from the nuclear waste solutions. Probes containing $^{137}$Cs [$H_2NB_2(C_6F_5)_6$], $^{137}$Cs[$B(C_6F_5)_4$], or $^{137}$Cs[$H(HO)_2B_2(C_6F_5)_6$] salts are considered particularly useful, since they allow the radioactive $^{137}$Cs isotope to become most easily and selectively isolated from the nuclear fuel reprocessing fluids. The isolated compounds allow further salts such as $^{137}$CsA (A e.g. Cl or Br) to be prepared pure by treating Cs[FAB] (FAB=$H_2NB_2(C_6F_5)_6$, $B(C_6F_5)_4$, $H(HO)_2B_2(C_6F_5)_6$) with the anhydrous acid HA so such pure salts $^{137}$CsA may be used as well for the therapy.

(c) Cancer brachytherapy

Probes containing radioactive $^{131}$Cs samples (half-life time t½=9.2 days) may be used for cancer brachytherapy, in particular for prostate and lung cancers. In radiopharmacy, $^{131}$Cs seeds for cancer brachytherapy (e.g., of prostate cancer) are prepared by irradiation of an aqueous $^{130}$Ba$^{2+}$ solution with a neutron flux to produce $^{131}$Cs$^+$ which is to be removed rapidly from the solution to avoid further neutron capture with generation of the strong gamma-emitter $^{132}$Cs. The complexes Cs[FAB], which are selective for Cs$^+$ and insoluble in water, allow immediate quantitative precipitation of $^{131}$Cs[FAB] and separation from the Ba$^{2+}$ isotopes by continuous cyclization of the reaction solution through a filter device, thereby avoiding further reaction to give $^{132}$Cs. The FAB separation is superior to the current at less efficient crown ether separation techniques as described in U.S. Pat. No. 8,270,554B2.

Technical Applications

In the nuclear fuel reprocessing, as part of the PUREX process or related processes, an acidic fluid is obtained which contains radioactive $^{137}$Cs$^+$ as a major fission product, together with $^{90}$Sr$^{2+}$, both of which are very strong gamma emitters. Applying [M$^I$(solv)][$H_2NB_2(C_6F_5)_6$], [M$^I$(solv)][$B(C_6F_5)_4$], or $(H_2O)_nB(C_6F_5)_3$ affords immediate selective precipitation of $^{137}$Cs[$H_2NB_2(C_6F_5)_6$], $^{137}$Cs[$B(C_6F_5)_4$], or $^{137}$Cs[$H(HO)_2B_2(C_6F_5)_6$] which are collected by filtration. The radioactive compounds are stored in proper encasings for transport and save handling. Possible usage is for sterilization of waste water sewage, food, packings, clean rooms, surgical instruments, and usage as gauges for monitoring purposes, abrasion control of furnace.

The invention is further illustrated by the attached Figures and Examples.

In the Figures, it is shown:

FIG. 1: the conformation of the inventive Cs complex (2)

Figure 2:
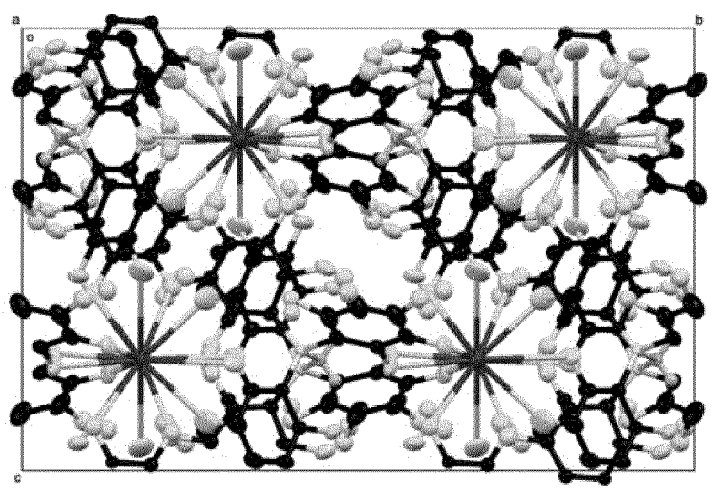

FIG. 2: the unit cell of the inventive Cs complex (2)

Figure 3:
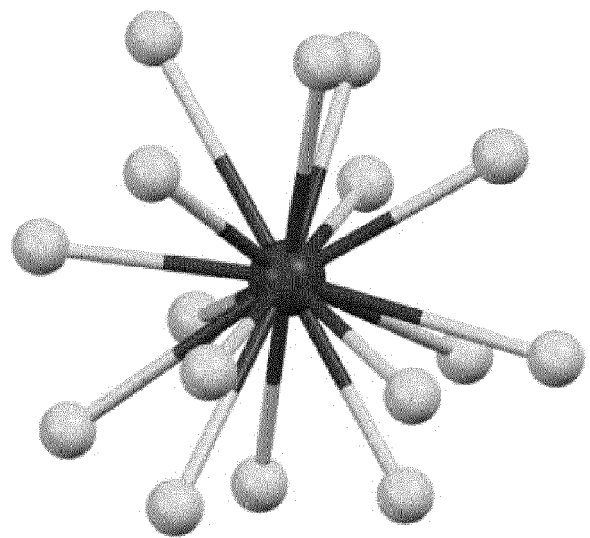

FIG. 3: the CsF$_{16}$ coordination in the inventive Cs complex (2)

Figure 4:
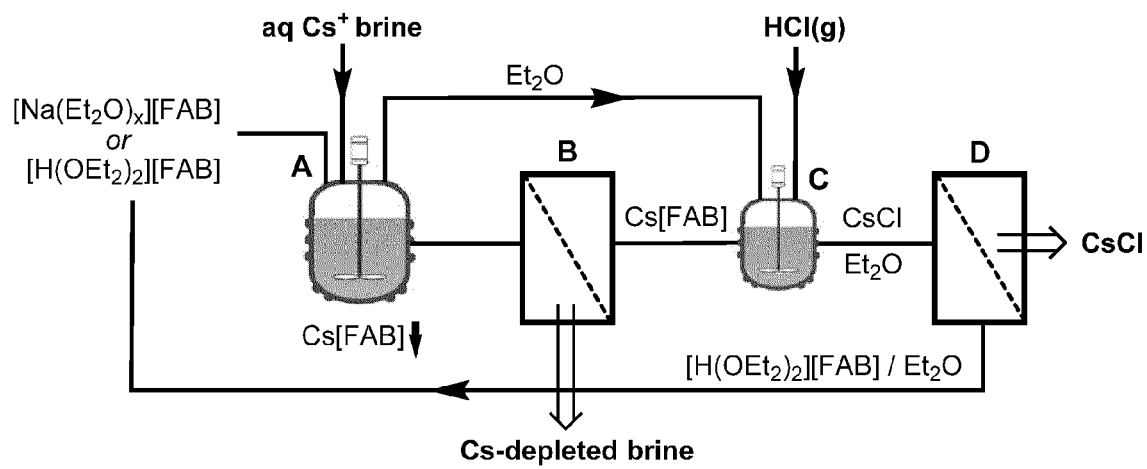

FIG. 4: a flowchart for the "FAB process" for the exploitation of cesium-containing mineral brines (FAB=fluoroarylboronate anion)

Figure 5:
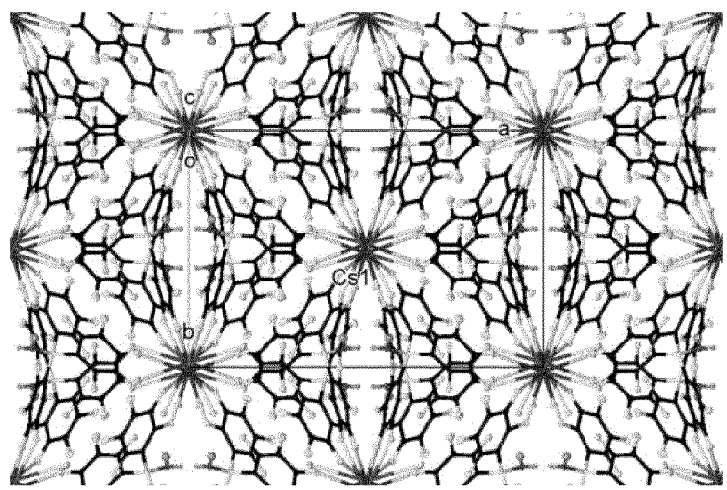

FIG. 5: the unit cell of the Cs complex Cs[$H(HO)_2B_2(C_6F_5)_6$] (5)

Figure 6:
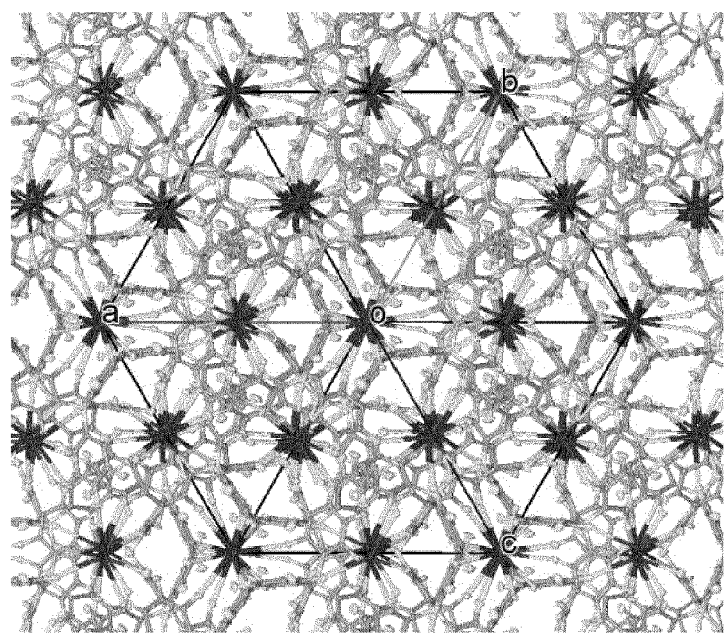

FIG. 6: the unit cell of the inventive complexes M[$B(C_6F_5)_4$] with M being Rb (8) or Cs (7).

The interest of the inventors in weakly coordinating anions (WCAs) has led them to synthesize the new cesium salt, Cs[$H_2NB_2(C_6F_5)_6$] (2). The inventors realized that (2) is insoluble in water and that it is instantaneously formed by mixing any aqueous solution containing Cs$^+$ with virtually any source of the [$H_2NB_2(C_6F_5)$]$^-$ anion. The reaction is 100% specific for Cs$^+$, since only in this case [$H_2NB_2(C_6F_5)_6$]$^-$ changes its usual asymmetric conformation to an "inverse C$_2$ symmetric" conformation to form a specific 3D lattice. The X-ray structure of (2) reveals that in the crystal 16 F atoms of five [$H_2NB_2(C_6F_5)_6$]$^-$ anions surround the Cs$^+$ cation, which corresponds to a record-setting Werner coordination number of CN=16 for any ligand element, including hydrogen, as represented in FIG. 1 to 3.

In the CsF$_{16}$ structure of (2), the largest and least electrophilic monoatomic cation is combined with a (perfluoroaryl)boronate (FAB) WCA of extremely low basicity, paired with high hydrophobicity. The low electrophilicity entails a low solvation enthalpy of Cs$^+$, and so the perfectly fitting WCA can compete with the water at Cs$^+$ on electrostatic grounds. Because of the weak and long Cs$^+$ . . . F coordination bonds the coordination sphere is large; thus, many F atoms can interact with Cs$^+$. The high number of cation-anion interactions stabilizes the given 3D network. Based on these findings a cyclic process for the extraction of cesium has been developed by the inventors which process enables quantitative extraction of cesium from water or acidic solutions which may contain Cs$^+$ in concentrations as low as a few ppm. FIG. 4 gives a flowchart for the process. By reacting the Cs$^+$ containing aqueous brine with [M$^I$(solv)]$^+$

[FAB]⁻ (1) (here: FAB=H$_2$NB$_2$(C$_6$F$_5$)$_6$) as a reagent in a stoichiometric amount, the polymeric, insoluble, and solvent-free Cs[H$_2$NB$_2$(C$_6$F$_5$)$_6$] (2) precipitates or can be extracted (A). Remarkably, once (2) is isolated from the aqueous brine (B), it can be cleaved, e.g., by HCl gas in diethyl ether (OEt$_2$) to quantitatively precipitate pure CsCl, with recovery of the FAB WCA in the form of [H(OEt$_2$)$_2$]$^+$ [FAB]$^-$ (C, D). Feeding [H(OEt$_2$)$_2$]$^+$[FAB]$^-$ back to an aqueous Cs$^+$ brine and evaporating the organic solvent allows for a cyclic process in which Cs$^+$ is 100% selectively and quantitatively extracted from any aqueous or acidic Cs$^+$ solution and converted into, e.g., pure CsCl without formation of byproducts.

For selective separation of rubidium from a mineral brine containing both Cs$^+$ and Rb$^+$, a tandem process can be envisaged. In the first step of FIG. 4, Cs$^+$ is extracted by the [H$_2$NB$_2$(C$_6$F$_5$)$_6$]$^-$ or [H(HO)$_2$B$_2$(C$_6$F$_5$)$_6$]$^-$ anions to obtain the Cs-depleted brine (stage B). For this brine, which still contains Rb$^+$, the process according to FIG. 4 is repeated, now with Li[B(C$_6$F$_5$)$_4$] as the extracting reagent. This second extracting step allows to selectively and nearly quantitatively precipitate Rb[B(C$_6$F$_5$)$_4$]. Reaction of the latter with an anhydrous acid in ethereal solution affords precipitation of, e.g., pure RbCl together with the recycled anion in ethereal solution.

By a tandem set-up of two cycles of the given flowchart as shown in FIG. 4, the first cycle with [H$_2$NB$_2$(C$_6$F$_5$)$_6$]$^-$ or [H(HO)$_2$B$_2$(C$_6$F$_5$)$_6$]$^-$ as an extracting anion for Cs$^+$ and the second with [B(C$_6$F$_5$)$_4$]$^-$ as the extracting anion for Rb$^+$, any brine containing, inter alia, Cs$^+$ and Rb$^+$ (but free from Tl$^+$) may be exploited for these elements in a cyclic process, allowing selective and quantitative isolation of pure salts CsA and RbA. The inventors suggest the term "FAB process" for referring to the Cs$^+$ and Rb$^+$ extraction by fluoroarylboronate anions.

EXAMPLES

Preparation Example 1—Synthesis of Extracting Reagent [Na(Et$_2$O)$_x$][H$_2$NB$_2$(C$_6$F$_5$)$_6$]

Sodium amide, NaNH$_2$ (3.9 g, 0.10 mol), and perfluorotriphenylborane, B(C$_6$F$_5$)$_3$ (105 g, 0.205 mol), mixed in 1.0 L of diethyl ether, are stirred until all NaNH$_2$ is dissolved. The solution contains 0.10 mol of dinuclear [Na(Et$_2$O)$_x$] [H$_2$NB$_2$(C$_6$F$_5$)$_6$] and is used for the cesium separation process.

Preparation Example 2—Synthesis of Extracting Reagent (C$_6$F$_5$)$_3$B(OH$_2$)$_n$ from (C$_6$F$_5$)$_3$B and Water (C$_6$F$_5$)$_3$B is a well-established strong Lewis-acid. It is known that (C$_6$F$_5$)$_3$B forms various hydrates with up to three molecules of water, (C$_6$F$_5$)$_3$B(OH$_2$)$_n$ (n=1-3). While (C$_6$F$_5$)$_3$B is air-sensitive, this is not the case for (C$_6$F$_5$)$_3$B (OH$_2$)$_n$. The inventors have found it most convenient to prepare the adduct for n=1 and use it for the reactions. (C$_6$F$_5$)$_3$B (51.2 g, 0.1 mol) was dissolved in 1 L of petrol ether (pentane), and water (1.8 mL, 0.1 mol) was added at ambient temperature. The mixture was stirred until a clear solution was obtained, if necessary by heating to reflux. When cooled, colorless (C$_6$F$_5$)$_3$B(OH$_2$) precipitated which was isolated by filtration and dried by air or vacuum; yield of the product is quantitative (53 g). The process can be carried out batchwise or continuously in the recovered solvent.

In the inventive process any typical aqueous solution of cesium salts can be used, largely irrespective of further cations and the type of anions. The solution may be industrial brine obtained from mineral digestion or wastewaters, but must have been freed from insoluble material. There appears to be no explicit pH dependency, but acidic to neutral solutions are preferred. Separate procedures are described for laboratory scale and technical preparations of CsCl in cyclic processes.

Example 1—Synthesis of Cs[H$_2$NB$_2$(C$_6$F$_5$)$_6$] (2)

All operations were performed under argon. A two-necked round bottom flask, equipped with a reflux condenser, was filled with [Na(OEt$_2$)$_4$][H$_2$NB$_2$(C$_6$F$_5$)$_6$] (2.72 g, 2.00 mmol), CsF (0.32 g, 2.1 mmol), and CH$_2$Cl$_2$ (50 mL). The flask was placed in an ultrasonic bath and the suspension sonicated for 14 h; by cooling the bath the temperature was kept at 40° C. The excess of CsF and the precipitated NaF were removed by filtration and the volume of the solution was reduced to about 25 mL. Admixing pentane to the solution afforded separation of colorless crystals; yield 1.74 g (74%).

$^1$H NMR (CD$_2$Cl$_2$): δ 5.66 (broad, NH$_2$). $^{11}$B NMR (CD$_2$Cl$_2$): δ–8.2 (s). $^{19}$F NMR (CD$_2$Cl$_2$): δ–132.8 (d, 2C, F$_{ortho}$), –160.1 (t, 1C, F$_{para}$), –165.6 ("t", 2C, F$_{meta}$). ESIpos MS (CH$_2$Cl$_2$): m/z (%)=133 ([Cs]$^+$, 100). ESIneg MS (CH$_2$Cl$_2$): m/z (%)=528 ([H$_2$NB(C$_6$F$_5$)$_3$]$^-$, 2), 1040 ([H$_2$NB$_2$(C$_6$F$_5$)]$^-$, 100).

Anal. Calcd for C$_{36}$H$_2$B$_2$CsF$_{30}$N (1172.9): C, 36.87; H, 0.17; B, 1.84; Cs, 11.33; F, 48.59; N, 1.19. Found: C, 36.77; H, 0.10; B, 1.64; Cs, 10.29; F, 47.15; N, 2.19.

Example 2—Isolation of Cs[H$_2$NB$_2$(C$_6$F$_5$)$_6$] (2)

(a) Form Neat Water

[Na(OEt$_2$)$_3$][H$_2$NB$_2$(C$_6$F$_5$)$_6$] (69.6 mg, 0.0541 mmol; FW=1285.4; c≈0.9·10$^{-4}$ M) was dissolved in 570 mL of water. CsCl (9.5 mg, 0.0564 mmol; FW=168.4) was added and after brief mixing the clear solution was left unstirred. Soon colorless crystals began to separate. The mixture was left overnight and the precipitate was isolated by filtration; yield of 2 42.1 mg (0.0359 mmol, 66%; FW=1172.9). The aqueous mother liquor was extracted once with 20 mL of CH$_2$Cl$_2$. Evaporation of the solvent gave an additional crop of 20 mg (0.0170 mmol, 32%). Total isolated yield was 62.1 mg (0.053 mmol; 98%). The IR spectra of the isolated solids were identical with that of pure Cs[H$_2$NB$_2$(C$_6$F$_5$)$_6$] (2).

(b) Water, Containing Other Metal Salts

To a water solution (450 mL), containing the inorganic salts listed below, was added [Na(OEt$_2$)$_3$][H$_2$NB$_2$(C$_6$F$_5$)$_6$] (27.5 mg, 0.0214 mmol; FW=1285.4; c≈4.75·10$^{-5}$ M) and the suspension was stirred overnight. A brown precipitate resulted (color presumably arising from Fe(OH)$_3$) which was filtered off and was washed with dichloromethane to extract 2. The solvent of the extract was evaporated to dryness to leave a colorless residue: yield 19.2 mg of 2 (0.0163 mmol, 76%; FW=1172.9), identified by comparison of the IR spectrum with that of pure 2. The experiment showed that 2 can be isolated selectively and in relatively high yield from a dilute aqueous solution containing a variety of other cations.

List of Added Inorganic Salts

| Salt | FW | mass [mg] | mass [mmol] | concentration [mol/L] |
|---|---|---|---|---|
| CsCl | 168.4 | 3.8 | 0.0226 | $5 \cdot 10^{-5}$ |
| KCl | 74.6 | 138.1 | 1.850 | $4.1 \cdot 10^{-3}$ |
| $PbCl_2$ | 278.1 | 121.3 | 0.436 | $1.0 \cdot 10^{-3}$ |
| $CrCl_3 \cdot 6H_2O$ | 266.4 | 66.3 | 0.249 | $0.55 \cdot 10^{-3}$ |
| $CaCl_2$ | 111 | 92.4 | 0.832 | $1.85 \cdot 10^{-3}$ |
| $FeCl_3 \cdot 6H_2O$ | 270.3 | 109.0 | 0.403 | $0.9 \cdot 10^{-3}$ |

Example 3—Synthesis of $Cs[(C_6F_5)_3B(O_2H_3)B(C_6F_5)_3]$ (5) (Eq. 4)

$B(C_6F_5)_3$ (5.12 g, 10.0 mmol) is treated in an inert solvent (hexane, toluene, $CH_2Cl_2$) with one equivalent of water (180 mg, 10.0 mmol) to give $(C_6F_5)_3B(OH_2)$ 4 as a colorless precipitate (4.80 g, 90%) which is isolated by filtration. Stirring $(C_6F_5)_3B(OH_2)$ 4 (2.65 g, 5.00 mmol) in 50 ml of water with CsCl (420 mg, 2.50 mmol) for 1 hour results in conversion of the solid into $Cs[(C_6F_5)_3B(O_2H_3)B(C_6F_5)_3]$ 5 (2.80 g, 94%), containing traces of water only. The reaction may also be carried out as a one-pot reaction, starting from $B(C_6F_5)_3$, CsCl and water.

Example 4—Preparation of $[Na(PEG-400)_n][H_2NB_2(C_6F_5)_6]$ for Oral Administration Polyethylene glycol 400 (PEG-400, Alfa Aesar) represents a polyethylene glycol mixture of average formula $H(OC_2H_4)_{8.67}(OH)$ (FW=400).

(a) The clear solution of $[Na(Et_2O)_3][H_2NB_2(C_6F_5)_6]$ (12.85 g, 10.0 mmol) in 50 mL of dichloromethane is treated with PEG-400 (3.55 mL, 10.0 mmol) and the same volume of pentane is added. In the course of several days colorless needles separate which were analyzed as $[Na(PEG-400)][H_2NB_2(C_6F_5)_6]$. Full removal of all volatiles from the mother liquor by vacuum leaves an additional colorless solid of same composition; total yield is quantitative.

(b) The solution of $[Na(Et_2O)_3][H_2NB_2(C_6F_5)_6]$ (12.85 g, 10.0 mmol) in 50 mL of dichloromethane is treated with PEG-400 (10.0 mL), 28.2 mmol). All volatiles are removed in a vacuum. The remaining liquid is extracted with 50 mL of pentane and the upper pentane phase is discarded. The lower phase is freed from residual pentane under vacuum to leave a colorless oil which has been analyzed for $[Na(PEG-400)_{\approx 2.7}][H_2NB_2(C_6F_5)_6]$; yield is quantitative. Both the solid and the liquid formulations of $[Na(PEG-400)_n]^+$ $[FAB]^-$ are ready for oral administration to the patient.

Example 5—Stepwise Laboratory Process for Cesium Separation

Step 1

5.0 L of a 0.01 M aqueous solution of ionic cesium (0.05 mol) is combined with 500 mL of a 0.10 M solution of $Na[H_2NB_2(C_6F_5)_6]$ (0.05 mol) in diethyl ether. By raising the temperature to 50° C. diethyl ether is distilled off. A colorless precipitate of $Cs[H_2NB_2(C_6F_5)_6]$ (55.7 g, 0.0475 mmol) is formed in the aqueous phase, which is isolated by filtration and washed with 20 mL of pure water. Crystallization of some residual $Cs[H_2NB_2(C_6F_5)_6]$ from the aqueous phase may be retarded. If desired, complete removal of cesium is achieved by extraction with diethyl ether. Otherwise, the aqueous phase is discarded. The recycled diethyl ether is best stored over $Na_2CO_3$ for complete removal of moisture; it can be used in step 2.

Step 2

The isolated $Cs[H_2NB_2(C_6F_5)_6]$ is re-dissolved in 500 mL of dry diethyl ether and treated with HCl gas (1.23 L of gas, 0.05 mol). Immediately, a colorless precipitate of CsCl (8 g, 0.0475 mol) is formed, which is separated by filtration and washed with some pure solvent. The precipitated microcrystalline CsCl is dried and stored as the isolated product or re-dissolved in a suitable solvent for further reaction. Purity of the isolated CsCl is about 99% (IR, NMR).

The ethereal filtrate contains intermediately formed $[H(OEt_2)_2][H_2NB_2(C_6F_5)_6]$ (0.0475 mol) and some HCl gas. The filtrate can be directly used for the next reaction cycle, starting with step 1. Possible loss of $[H_2NB_2(C_6F_5)_6]$ in each reaction cycle, estimated to amount to about 1%, is to be replaced for the next cycle.

Example 6—Process for Cs-Recovery

Method 1 (from Concentrated $Cs^+$ Brine, Involving Intermediate $Cs[H_2NB_2(C_6F_5)_6]$ Isolation)

1.0 L of a 0.2 M aqueous brine of $Cs^+$ (0.2 mol Cs), e.g., from mineral digestion, is combined with 2.0 L of a 0.1 M $[Na(OEt_2)_4][H_2NB_2(C_6F_5)_6]$ diethyl ether or MTBE solution (0.2 mol of reagent). The mixture is stirred and the organic solvent is distilled off. When the ether is removed and collected, pure $Cs[H_2NB_2(C_6F_5)_6]$(175-200 g, 0.15-0.17 mol) precipitates from the aqueous phase. Precipitation may occur slowly so some resting time is advisable to increase the yield. The precipitated $Cs[H_2NB_2(C_6F_5)_6]$ is separated by filtration and washed with some clear water and dried with air or under vacuum. (The yield may be increased to quantitative by extracting the aqueous phase as described in method 2.) The collected ether is dried over $Na_2CO_3$. $Cs[H_2NB_2(C_6F_5)_6]$ is dissolved in said dried ether and the obtained solution is treated with gaseous HCl (4.9 L, 0.2 mol). Thereby, pure CsCl precipitates in nearly quantitative yield (25-29 g, 0.15-0.17 mol). CsCl is isolated by filtration, washed with ether, and dried under vacuum. The ethereal solution, containing $[H(OEt_2)_2][H_2NB_2(C_6F_5)_6]$ and excess HCl, can be used for a further reaction cycle. Excess of acid can be neutralized with $Na_2CO_3$.

Method 2 (from dilute $Cs^+$ solutions without separation of $Cs[H_2NB_2(C_6F_5)_6]$)

5.0 L of a 0.01 M aqueous solution of $Cs^+$, e.g., obtained from radiocesium reprocessing and containing a total amount of 0.05 mol Cs, is combined with 500 mL of 0.1 M diethyl ether solution of $[Na(OEt_2)_4][H_2NB_2(C_6F_5)_6]$ reagent (0.05 mol). The emulsion formed in the beginning is stirred for 30 min. After some resting time the ethereal phase is carefully separated from the aqueous phase. The aqueous phase has been nearly fully depleted from $Cs^+$ and is discarded. The ethereal phase contains dissolved $Cs[H_2NB_2(C_6F_5)_6]$ and is treated with 5 g of $Na_2CO_3$ for removal of moisture. After separation from the desiccant by filtration, gaseous hydrogen chloride (1.23 L, 0.05 mol) is added to the solution, whereupon colorless CsCl precipitates (7.58-8.42 g, 0.045-0.05 mol). The product is separated by filtration, washed with dry ether, and dried under vacuum. Purity is about 99% (IR, NMR, MS). The ethereal solution, containing $[H(OEt_2)_2][H_2NB_2(C_6F_5)_6]$ and excess HCl, can be used for a further reaction cycle. Part of the $Na_2CO_3$ may be used for neutralizing the aqueous waste solution.

Example 7—Process for Cs Recovery Based on $B(C_6F_5)_3$ 5.0 L of a 0.01 M aqueous solution of $Cs^+$ (0.05 mol Cs), is stirred with solid $(C_6F_5)_3B(OH_2)$ (53 g, 0.10 mol) for 6 hours. The colorless precipitate is isolated by filtration and dried to yield 55 g (0.046 mmol) of $Cs[(H_3O_2)B_2(C_6F_5)_6]\cdot 0.1H_2O$. The compound may contain a trace of water. The compound is dissolved in 1 L of dry diethyl ether and treated with 1.2 L (0.049 mmol) of gaseous HCl. Immediately, a precipitate of CsCl (7.7 g, 0.045 mmol) is formed which is isolated by filtration. The ether filtrate contains recovered $(C_6F_5)_3B(OH_2)_n$ and any excess of HCl and can either be evaporated to dryness to recover solid $(C_6F_5)_3B(OH_2)_n$ (n=1-3) or be fed back as a solution for the next reaction cycle.

Example 8—Cyclic Process for Cs Recovery

As shown in the scheme of FIG. 4, the aqueous or acidic $Cs^+$ brine is treated in the mixer A with starting Na[FAB] dissolved in some ether ($Et_2O$ or MTBE); the ethereal solvent is distilled off and Cs[FAB] precipitates quantitatively. In separator B the precipitated Cs[FAB] is isolated (by filtration or centrifuge) and dried (airstream); the $Cs^+$-depleted brine is discharged for other uses. In the small mixer C the isolated Cs[FAB] is redissolved in the ether distilled from A, and the concentrated solution is treated with HCl gas to precipitate CsCl. The product slurry is transferred to separator D for isolation of pure CsCl; the ether filtrate containing pure $[H(OEt_2)_2][FAB]$ (or MTBE solvate) is fed back to mixer A. Thus, besides the recycled stocks of [FAB] reagent and ether solvent, the only reagents which are consumed are the extracted $Cs^+$ and the equimolar amount of HCl gas. In addition to gaseous HCl, the process is expected to work equally well with other non-aqueous acids such as HBr, $H_2SO_4$, RCOOH etc. to afford the corresponding Cs salts.

SUMMARY

As illustrated before, the present invention allows various applications. There are numerous applications conceivable for the FAB process, notably for Cs:
(a) Exploitation of Cs and Rb minerals. The FAB process avoids the otherwise numerous recrystallizations, handlings of large volumes, and environmental problems associated with current industrial processing of Cs and (less important) Rb.
(b) Environmental issues. Viewing at current cesium production, full removal of $Cs^+$ is a pressing problem because of environmental reasons. Using FAB reagents as an additive to a final settling basin for the brine will allow quantitative sedimentation of Cs[FAB] and Rb[FAB] and full exploitation of the contained Cs and Rb.
(c) $^{134/135/137}Cs$ Fission Product Extraction (FPEX). Nuclear fuel reprocessing occurs by the PUREX and UREX processes. In the joined FPEX process, $^{134/135/137}Cs^+$ is currently apparently extracted by chlorinated cobalt bis (dicarbollide), $[CCD]^-$. Cs[FAB] extraction appears superior to current Cs[CCD] extraction, since the FAB reagents are more readily available, more selective, and only a single separation step is necessary, which simplifies the process, reduces costs and waste, and allows for saver execution.
(d) $^{137}Cs$ technical and radiophamaceutical applications. The FAB process should allow ready preparation of pure $^{137}Cs[FAB]$ and other $^{137}CsA$ radioisotope compounds by the modified FPEX process (see c) and easier handling of the compounds. Typical commercial applications for $^{137}CsA$ compounds are, inter alia, sewage sludge sterilization, furnace lining controlling, and cancer afterloading therapy.
(e) $^{131}Cs$ radiophamaceuticals. $^{131}Cs$ (t½=9.7 d) is used for cancer seed implantation (brachytherapy). For this purpose, $^{131}Cs$ is prepared by treating an aqueous $^{130}Ba^{2+}$ solution with neutrons to afford $^{131}Ba$, which transforms into $^{131}Cs$. The (slowly formed) $^{131}Cs$ must be continuously removed to avoid further neutron capture to give $^{132}Cs$. Precipitating $^{131}Cs^+$ with $[FAB]^-$ in aqueous solution is expected to allow for fast, quantitative, and continuous separation of pure $^{131}Cs[FAB]$ from $^{130/131}Ba^{2+}$.
(f) $^{134/135/137}Cs$ decontamination. Waste waters from nuclear plants or discharges form nuclear plant accidents containing $^{134/135/137}Cs$ loadings can be reprocessed, with Cs[FAB] separation being effective down to the ppm level. $^{134/135/137}Cs$ decontamination of humans or mammals is also conceivable, challenging the current Prussian blue therapy.

Therefore, the present invention is also directed to the following embodiments:
It is claimed that compounds of types 1, 3, 4 and 6 can be used to precipitate $Cs^+$ ions from aqueous solutions, containing $Cs^+$ in low concentrations ($10^{-5}$ molar or lower, such as 10 ppm);
It is claimed that such precipitation allows removal of Cs-134/135/137 from radioactive waste waters in >75% yields. Extraction of such treated solutions with $CH_2Cl_2$, after or in place of the cesium salt precipitation, allows nearly quantitative separation of Cs-134/135/137 from waste solutions;
It is claimed that such removal is specific for cesium;
It is claimed that in particular compounds of type 1 can be used as an antidote for Cs-134/135/137 contamination of humans and animals, without uptake by the body or development of harmful side-effects (except minor effects such as constipation);
It is claimed that the suggested therapy, in its administration regimen, corresponds largely to the PB therapy, but is more effective;
It is claimed that compounds of type 2, 5, and 7, in particular those of type 2, can be prepared containing radioactive isotopes Cs-131 and Cs-137 and that these compounds have a favorable profile for use in therapy of various cancers. The advantage of such compounds is given by insolubility in water and easy preparation by precipitation from aqueous solutions.

The invention claimed is:
1. A pharmaceutical composition comprising a complex of the formula $[M^I(solv)]^+L^-$, wherein:
$M^I$ is selected from $H(OH_2)_n$, Li, Na, K, ½Mg, MgY, Mg(OH), ½Ca, Ca(OH), wherein Y is a halide,
(solv) represents a solvating ligand capable of coordinating to $M^I$,
$L^-$ is $[(C_6F_5)_3B—X—B(C_6F_5)_3]^-$, and
wherein X is selected from halide, $OH^-$, or $NH_2^-$.
2. A method for treating and/or preventing radiation damage, or for counteracting contamination with radioactive isotopes, or for treating Tl-poisoning, said method comprising administering to a patient in need thereof an effective amount therefor of a complex according to claim 1.
3. Complex of the formula $[M^I]^+L^-$, wherein:
$M^I$ is Cs, and
$L^-$ is $[(C_6F_5)_3B—X—B(C_6F_5)_3]^-$,
wherein X is selected from halide, $OH^-$, $O_2H_3^-$ or $NH_2^-$.

4. Complex of the formula [M$^I$]$^+$L$^-$,
wherein
M$^I$ is Cs in the form of a radioactive isotope, and
L$^-$ is [(C$_6$F$_5$)$_3$B—X—B(C$_6$F$_5$)$_3$]$^-$,
wherein X is selected from halide, OH$^-$, O$_2$H$_3^-$ or NH$_2^-$.

5. Process for preparing a complex of the formula [M$^I$]$^+$L$^-$ according to claim 4, wherein:
M$^I$ is Cs, and
L$^-$ is [(C$_6$F$_5$)$_3$B—X—B(C$_6$F$_5$)$_3$]$^-$,
   wherein X is selected from halide, OH$^-$, O$_2$H$_3^-$ or NH$_2^-$,
wherein the process comprises reacting a complex of the formula [M$^I$(solv)]$^+$L$^-$, wherein:
M$^I$ is selected from H(OH$_2$)$_n$, Li, Na, K, ½Mg, MgY, Mg(OH), ½Ca, Ca(OH), wherein Y is a halide,
(solv) represents a solvating ligand capable of coordinating to M$^I$, and
L$^-$ is [(C$_6$F$_5$)$_3$B—X—B(C$_6$F$_5$)$_3$]$^-$,
wherein X is selected from halide, OH$^-$, O$_2$H$_3^-$ or NH$_2^-$ and Y is a halide,
with a Cs salt in an aqueous medium.

6. A method of treating a tumor disease, said method comprising administering to a patient in need thereof an effective amount therefor of a complex according to claim 4.

7. A method of conducting brachytherapy or afterload therapy, said method comprising administering to a patient in need thereof an effective amount therefor of a complex according to claim 4.

8. A method of sterilizing waste water sewage, food, packings, clean rooms, and construction monitoring purposes using a complex according to claim 3.

9. Method of using a complex of the formula [M$^I$(solv)]$^+$L$^-$, wherein:
M$^I$ is selected from H(OH$_2$)$_n$, Li, Na, K, ½Mg, MgY, Mg(OH), ½Ca, Ca(OH), wherein Y is a halide,
(solv) represents a solvating ligand capable of coordinating to M$^I$, and
L$^-$ is [(C$_6$F$_5$)$_3$B—X—B(C$_6$F$_5$)$_3$]$^-$,
wherein X is selected from halide, OH$^-$, O$_2$H$_3^-$ or NH$_2^-$, for the removal of Cs or Rb from aqueous liquids.

10. A process for separating cesium from a cesium containing aqueous fluid,
wherein the process comprises either Sequence I or Sequence II, wherein Sequence I is:
a. reacting a complex of the formula [M$^I$(solv)]$^+$L$^-$, wherein M$^I$ is selected from Li, Na, K, ½ Mg, Mg(OH), ½ Ca, Ca(OH), (solv) represents a solvating ligand capable of coordinating to M$^I$, and L$^-$ is [(C$_6$F$_5$)$_3$B—X—B(C$_6$F$_5$)$_3$]$^-$, wherein X is selected from halide, O$_2$H$_3^-$ or NH$_2^-$, with a cesium containing aqueous fluid, whereby a complex of the formula Cs$^{I+}$L$^-$ is precipitated from the aqueous solution;
b. separating the precipitated complex of the formula Cs$^{I+}$L$^-$ from the aqueous phase and drying the obtained precipitated complex of the formula Cs$^{I+}$L$^-$;
c. dissolving the separated complex of the formula Cs$^{I+}$L$^-$ in an anhydrous organic solvent selected from a dialkyl ether R$_2$O and alcohol ROH wherein R is C$_1$ to C$_6$;
d. treating said organic solvent containing the complex of the formula Cs$^{I+}$L$^-$ with an anhydrous acid HA, where HA is HCl, HBr, H$_2$SO$_4$, H$_3$PO$_4$ or a compound R$_A^-$H$^+$, in which R$_A^-$ is a carboxylic acid residue and R$_A^-$ is sufficiently basic to form an ion-pair CsR$_A$, whereby CsA is precipitated, and separating the precipitated CsA from said organic solvent; and
e. recycling said organic solvent containing a complex of the formula [M$^I$(solv)]$^+$L$^-$, wherein M$^I$ is H(OR$_2$)$_n$ and L$^-$ is [(C$_6$F$_5$)$_3$B—X—B(C$_6$F$_5$)$_3$]$^-$, to step a;
and the Sequence II is:
a. reacting a complex of the formula [M$^I$(solv)]$^+$L$^-$, wherein M$^I$ is selected from Li, Na, K, ½ Mg, Mg(OH), ½ Ca, Ca(OH), (solv) represents a solvating ligand capable of coordinating to M$^I$, and L$^-$ is [(C$_6$F$_5$)$_3$B—X—B(C$_6$F$_5$)$_3$]$^-$, wherein X is selected from halide, O$_2$H$_3^-$ or NH$_2^-$, in an organic solvent immiscible with water with a cesium containing aqueous fluid, whereby a complex of the formula Cs$^{I+}$L$^-$ is extracted from the aqueous solution into the organic solvent;
b. drying the obtained organic solvent containing the complex of the formula Cs$^{I+}$L$^-$;
c. treating said organic solvent containing the complex of the formula Cs$^{I+}$L$^-$ with an anhydrous acid HA, where HA is HCl, HBr, H$_2$SO$_4$, H$_3$PO$_4$ or a compound R$_A^-$H$^+$, in which R$_A^-$ is a carboxylic acid residue and R$_A^-$ is sufficiently basic to form an ion-pair CsR$_A$, whereby CsA is precipitated, and separating the precipitated CsA from said organic solvent; and
d. recycling said organic solvent containing a complex of the formula [M$^I$(solv)]$^+$L$^-$, wherein M$^I$ is H(OR$_2$)$_n$ and L$^-$ is [(C$_6$F$_5$)$_3$B—X—B(C$_6$F$_5$)$_3$]$^-$, to step a.

11. Process according to claim 10, wherein the organic solvent is an ether having 4 to 10 carbon atoms.

12. Process according to claim 10, wherein any amount of a Cs$^I$L$^-$ complex precipitated in step a. of Sequence I is transferred to the organic solvent by adding a sufficient amount of the organic solvent.

13. Process according to claim 10, wherein the cesium containing aqueous fluid is selected from brines obtained from digestion of cesium ores, used cesium containing drilling fluids, and fluids containing Cs-131 or Cs-134/135/137 isotopes, either as solutions from a synthesis process, a reprocessing process, or as wastewaters from atomic plant facilities.

14. Process for separating cesium and rubidium from an aqueous fluid, wherein the process comprises:
a. reacting a complex of the formula [M$^I$(solv)]$^+$L$^-$, wherein M$^I$ is selected from Li, Na, K, ½ Mg, Mg(OH), ½ Ca, Ca(OH), and L$^-$ is [XB$_2$(C$_6$F$_5$)$_6$]$^-$, wherein X is selected from halide, O$_2$H$_3^-$ or NH$_2^-$, with a Cs and Rb containing aqueous fluid whereby a complex of the formula Cs$^{I+}$L$^-$ is precipitated from the aqueous solution;
b. separating the precipitated complex of the formula Cs$^{I+}$L$^-$ from the aqueous phase and drying the obtained precipitated complex of the formula Cs$^{I+}$L$^-$;
c. dissolving the separated complex of the formula Cs$^{I+}$L$^-$ in an anhydrous organic solvent selected from a dialkyl ether R$_2$O and alcohol ROH wherein R is C$_1$ to C$_6$;
d. treating said organic solvent containing the complex of the formula Cs$^{I+}$L$^-$ with an anhydrous acid HA, where HA is HCl, HBr, H$_2$SO$_4$, H$_3$PO$_4$ or a compound R$_A^-$H$^+$, in which R$_A^-$ is a carboxylic acid residue and R$_A^-$ is sufficiently basic to form an ion-pair CsR$_A$, whereby CsA is precipitated, and separating the precipitated CsA from said organic solvent;
e. recycling said organic solvent containing a complex of the formula [M$^I$(solv)]$^+$L$^-$, wherein M$^I$ is H(OR$_2$)$_n$ and L$^-$ is [(C$_6$F$_5$)$_3$B—X—B(C$_6$F$_5$)$_3$]$^-$, to step a;
f. treating the aqueous phase obtained in step b. with M$^+$[B(C$_6$F$_5$)$_4$]$^-$, M being H, Li, Na, K, ½ Mg, Mg(OH), ½ Ca, Ca(OH), optionally solvated, whereby Rb[B(C$_6$F$_5$)$_4$] is selectively and almost quantitatively precipitated,
g. separating the precipitated complex of the formula Rb[B(C$_6$F$_5$)$_4$] from the aqueous phase and drying the obtained precipitated complex of the formula Rb[B(C$_6$F$_5$)$_4$]; and optionally
h. dissolving the separated complex of the formula Rb[B(C$_6$F$_5$)$_4$] in an anhydrous organic solvent selected from a dialkyl ether R$_2$O and alcohol ROH wherein R is C$_1$ to C$_6$;
i. treating said organic solvent containing the complex of the formula Rb[B(C$_6$F$_5$)$_4$] with an anhydrous acid HA, where HA is HCl, HBr, H$_2$SO$_4$, H$_3$PO$_4$ or a compound R$_A^-$H$^+$, in which R$_A^-$ is a carboxylic acid residue and R$_A^-$ is sufficiently basic to form an ion-pair RbR$_A$, whereby RbA is precipitated, and separating the precipitated RbA from said organic solvent;
j. recycling said organic solvent containing a complex of the formula [M$^I$(solv)]$^+$L$^-$, wherein M$^I$ is H(OR$_2$), and L$^-$ is [B(C$_6$F$_5$)$_4$]$^-$, to step f.

15. Process for preparing a complex of the formula [M$^I$]$^+$L$^-$ according to claim 4, wherein:
M$^I$ is Cs in the form of a radioactive isotope, and
L$^-$ is [(C$_6$F$_5$)$_3$B—X—B(C$_6$F$_5$)$_3$]$^-$,
wherein X is selected from halide, OH$^-$, O$_2$H$_3^-$ or NH$_2^-$,
wherein the process comprises reacting a complex of the formula [M$^I$(solv)]$^+$L$^-$, wherein:
M$^I$ is selected from H(OH$_2$)$_n$, Li, Na, K, ½ Mg, MgY, Mg(OH), ½ Ca, Ca(OH), wherein Y is a halide,
(solv) represents a solvating ligand capable of coordinating to M$^I$, and
L$^-$ is [(C$_6$F$_5$)$_3$B—X—B(C$_6$F$_5$)$_3$]$^-$,
wherein X is selected from halide, OH$^-$, O$_2$H$_3^-$ or NH$_2$ and Y is a halide,
with a Cs salt wherein Cs in the form of a radioactive isotope in an aqueous medium.

16. A method of sterilizing waste water sewage, food, packings, clean rooms, and construction monitoring purposes using a complex according to claim 4.

* * * * *